United States Patent [19]

McGill, III

[11] Patent Number: 5,578,713
[45] Date of Patent: Nov. 26, 1996

[54] ONE STEP PROCESS FOR PRODUCTION OF DIRITHROMYCIN

[75] Inventor: John M. McGill, III, Lafayette, Ind.

[73] Assignee: Eli Lilly and Company, Indianapolis, Ind.

[21] Appl. No.: 95,366

[22] Filed: Jul. 20, 1993

Related U.S. Application Data

[63] Continuation of Ser. No. 768,803, Sep. 30, 1991, abandoned.
[51] Int. Cl.$^6$ ........................................................ C07H 1/00
[52] U.S. Cl. ............................ 536/18.5; 536/7.2; 536/7.4
[58] Field of Search ............................. 536/7.2, 7.4, 18.5

[56] References Cited

U.S. PATENT DOCUMENTS

| | | | |
|---|---|---|---|
| 4,048,306 | 9/1977 | Maier et al. | 424/180 |
| 4,438,109 | 3/1984 | Umezawa et al. | 536/7.1 |
| 4,794,173 | 12/1988 | Umezawa et al. | 536/7.1 |

OTHER PUBLICATIONS

Counter et al, Antimicrobial Agents and Chemotherapy, Jun. 1991, pp. 1116–1121.

Luger and Maier, Molecular structure of 9–deoxy–11–deoxy–9–11–(imino(2–(2–methoxyethoxy) ethylidene)oxy)–(9S)–erythromycin, a new erythromycin derivative, *Journal of Crystal and Molecular Structure*, 9:329–338 (1979).

Dirithromycin, *Drugs of the Future* 14:112–115 (1989).

Firl et al., Epimerization of erythromycin derivatives, *Journal of Antibiotics* 43:1271–77 (1990).

Counter, et al., "Synthesis and Antimicrobial Evaluation of Dirithromycin", *Antimicrobial Agents and Chemotherapy*, vol. 35, No. 6, pp. 1116–1126, Jun., 1991.

*Primary Examiner*—Elli Peselev
*Attorney, Agent, or Firm*—Kathleen R. S. Page; Paul R. Cantrell; Joseph A. Jones

[57] ABSTRACT

The disclosure relates to a new process for the synthesis of the macrolide antibiotic dirithromycin in crystalline form. The process is carried out in a single reaction vessel whereby an acetal dissolved in acetonitrile, in the presence of an acid catalyst, is hydrolyzed to the related hemiacetal which then reacts directly with erythromycylamine to form crystalline dirithromycin.

22 Claims, No Drawings

ONE STEP PROCESS FOR PRODUCTION OF DIRITHROMYCIN

This application is a continuation of application Ser. No. 07/768,803, filed on Sep. 30, 1991, now abandoned.

BACKGROUND OF THE INVENTION

The present invention discloses a novel process for the synthesis of the macrolide antibiotic 9-deoxo-11-deoxy-9,11-{imino [2- (2-methoxyethoxy)ethylidene]oxy}-(9S)-erythromycin, hereinafter referred to as dirithromycin.

Dirithromycin is a derivative of and has a similar spectrum of activity to erythromycin. However, pharmacokinetic studies of dirithromycin summarized in Drugs of the Future, 14:112 (1989), reveal the antibiotic to have lower peak but longer-lasting serum levels than erythromycin in all species studied. Dirithromycin also has the advantageous property of rapid distribution of high concentrations of antibiotic activity to all tissues. These characteristics would be expected to make possible higher doses in the target organs.

Applicants have discovered that dirithromycin may be produced in an alternate manner to the aldehyde/erythromycylamine condensation reaction disclosed in previous reports. For example, Maier et al., in U.S. Pat. No. 4,048,306, which is herein incorporated by reference, reports that polar organic solvents are the preferred solvents for this reaction. More specifically, aqueous dioxane was used as the solvent for condensation of 2-(2-methoxyethoxy)acetaldehyde diethyl acetal and erythromycylamine in the presence of an acidic ion-exchange resin. Maier et al. states that an aldehyde is formed from hydrolysis of the acetal which presumably reacts in turn erythromycylamine to form the dirithromycin final product. Under the reaction conditions proposed by Maier et al., the dirithromycin product is soluble in the reaction mixture and therefore, must be isolated by evaporation of the solvent followed by chromatographic purification of the residue and recrystallization from ether/petroleum ether.

SUMMARY OF THE INVENTION

The current invention provides a one-pot process for producing crystalline dirithromycin. This process is much more efficient than previous processes, increasing the yield and purity of the final product and directly forming a pharmaceutically pure crystalline precipitate. The crystalline product can be easily separated from the reaction mixture, thereby simplifying purification and reducing the amount of waste byproducts. The new process also avoids the use of an ion-exchange resin which may impart impurities.

The current process stems from the discovery that an acetal dissolved in aqueous acetonitrile, in the presence of an acid catalyst, will be hydrolyzed to the related hemiacetal. The hemiacetal then reacts directly with erythromycylamine under the same conditions to form the cyclized dirithromycin.

The current invention provides a process for making crystalline dirithromycin wherein an acetal, represented by the formula

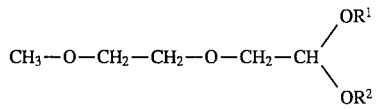

wherein $R^1$ and $R^2$ are straight or branched alkyl groups of one to about six carbon atoms which may be identical to or different from each other or together with each other may be —CH2—CH2—, —CH2—CH2—CH2—, or —CH2—CH2—CH2—CH2— thereby forming a 5-to 7-membered ring when taken in conjunction with the structure to which they are attached, is dissolved in aqueous acetonitrile, hydrolyzed over time in the presence of an acid catalyst to an equilibrium mixture, and reacted with erythromycylamine.

DETAILED DESCRIPTION OF THE INVENTION

The current invention provides a one-pot process for the synthesis of crystalline dirithromycin. The term one-pot is meant to indicate that intermediates necessary for the production of the final product need not be isolated before further reaction but are instead treated in the same reaction vessel to achieve synthesis of the final product. The current process includes the direct condensation of erythromycylamine with a hemiacetal that has been generated in situ by hydrolysis of the related acetal. The process also includes conditions where the final product is produced in a crystalline pharmaceutically pure form of relatively low solubility and, therefore, can be readily isolated from the reaction mixture by conventional methods such as, for example, filtration.

The consumption of the erythromycylamine, that is, conversion of the erythromycylamine to dirithromycin, is dependent upon those factors which affect the hydrolysis reaction as well as those factors which might independently affect the condensation reaction. Some of these same factors influence whether a crystalline product is formed as opposed to a soluble product which ultimately affects the value of this process.

First, with regard to hydrolysis of the acetal to the hemiacetal, the reaction is affected by the type of solvent which is used, the water content of the solvent, the type and amount of acid catalyst used, the structure and amount of the acetal, and the temperature at which the reaction is run. These factors determine the amount of hemiacetal that is produced and the time necessary for the reaction to reach an acetal/hemiacetal equilibrium, which in turn directly affect the yield and efficiency of the process.

Second, the condensation reaction, including the in situ crystallization of the final product, is specific for the solvent which is used and is directly affected by the amount of acid catalyst in the reaction mixture and the water content of the solvent. The conditions which affect only one reaction or the other may be adjusted to an optimum for that specific reaction without regard for the other reaction. Those conditions which affect both the hydrolysis and the condensation reactions must be adjusted to account for this dual effect. Accounting for effects on both reactions may be done either by establishing conditions which are a compromise between the two reactions, thereby optimizing the process as a whole, or by changing conditions within the reaction vessel over time such that they are optimized for the individual reactions of the process.

The process disclosed herein is particularly sensitive to the type of solvent which is used. First, few solvents facilitate ready hydrolysis of the acetal to the hemiacetal. Second, of the solvents which promote hydrolysis, very few allow the production of the dirithromycin product in a crystalline form. In order to satisfy the hydrolysis requirements and to obtain an insoluble crystalline product, acetonitrile is an especially preferred solvent.

The water content of the solvent produces a nonlinear quadratic effect on the amount of hemiacetal produced. The ratio of hemiacetal to acetal at equilibrium increases as the water content goes up but decreases once the water content exceeds about 6.67%.

The water content of the solvent also affects the condensation reaction. An increase in water content causes an increase in the solubility of the dirithromycin final product and therefore decreases the amount of crystalline dirithromycin which is recovered from the reaction mixture. Thus, a determination of water content tailored for optimal efficiency must consider both the hydrolytic reaction and the condensation reaction.

In order to balance the effects of aqueous content of the solvent during the hydrolysis reaction period and the effects during the final condensation reaction, a solvent having a water content between about 2% and about 10% is preferred, a water content between about 3% and about 5% is more preferred, and a water content of about 4% is most preferred.

The hydrolysis reaction is affected by both the type and amount of acid that is used as catalyst. Any acid in an amount which promotes the hydrolysis of acetal to hemiacetal and which does not itself react with the reagents may be suitable as a catalyst. The effect of several different acids on dimethyl acetal hydrolysis is shown in Table 1 which reports the apparent equilibrium constant ($K_{eq}$) for the hydrolysis. Sulfuric acid, methanesulfonic acid, p-toluenesulfonic acid, hydrochloric acid, and camphorsulfonic acid are preferred catalysts for the hydrolysis reaction. p-Toluenesulfonic acid routinely gave better yield and quality of dirithromycin product and is therefore an especially preferred catalyst for the process.

TABLE 1

| Acid | Apparent $K_{eq}$ |
| --- | --- |
| Sulfuric acid | 1.04 |
| Methanesulfonic acid | 1.03 |
| p-Toluenesulfonic acid | 1.09 |
| Hydrochloric acid | * |
| Camphorsulfonic acid | 0.85 |

*$K_{eq}$ not determined but hydrolysis products were formed

The amount of acid catalyst used displays a nonlinear effect on total hydrolysis of acetal to hemiacetal. In addition, the amount of acid catalyst used in the reaction is directly proportional to the speed at which the hydrolysis reaction reaches an acetal/hemiacetal equilibrium. Conversely, the amount of acid catalyst is inversely proportional to the isolated yield of dirithromycin. Establishing preferred levels of acid catalyst to be included in the process must consider all of these effects. In order to optimize the whole process, an acid catalyst content of less than about 0.2 equivalents is preferred. When using p-toluenesulfonic acid as catalyst, about 0.02 to about 0.10 equivalents is preferred and about 0.04 equivalents is most preferred. Amounts of reactants which are stated as equivalents (eq) throughout this disclosure are measured relative to the molar amount of erythromycylamine added to the reaction.

The temperature at which the hydrolysis reaction is run has a marked effect upon the time required to reach equilibrium but has little effect on the condensation reaction. Small increases in the temperature result in relatively large increases in the rate at which the hemiacetal is produced. However, increases in temperature also cause a decrease in the total amount of hemiacetal that is produced as a result of the hydrolysis. Consequently, during the hydrolysis portion of the process, temperatures ranging from 18° C. to 50° C. are preferred, while temperatures of 20° C. to 40° C. are more preferred, and temperatures of 22° C. to 30° C. are especially preferred.

The specific acetal which is used as a starting material also influences the hydrolysis reaction. Preferred acetals are 2-(2-methoxyethoxy)-acetaldehyde dimethyl acetal and 2-(2-methoxyethoxy)-acetaldehyde diethyl acetal. Under identical conditions, the apparent $K_{eq}$ for the hydrolysis of diethyl acetal was 1.52 as compared to 1.02 for dimethyl acetal. Thus, the process requires greater amounts of the smaller acetal in order to provide enough hemiacetal to allow total consumption of erythromycylamine.

PREPARATION 1

Crystalline dirithromycin—a condensation product of 2-(2-methoxyethoxy)acetaldehyde dimethyl acetal and erythromycylamine Several reactions were conducted according to the following general scheme. 2-(2-Methoxyethoxy)-acetaldehyde dimethyl acetal was placed in a three-neck flask equipped with a mechanical stirrer and was then dissolved in 15 ml of aqueous acetonitrile containing p-toluenesulfonic acid. The mixture was stirred under a nitrogen atmosphere for 20 hours at 23° C. Erythromycylamine (5 g, 1 eq) was added over a 20 minute period and stirring continued for 12–16 hours at 23° C. The reaction mixture was cooled to 0° C. for two hours and then filtered to recover dirithromycin crystals. The crystals were washed with cold acetonitrile and dried in vacuo at 40° C. Specific reaction conditions and reagents are detailed in Table 2 which also includes the yield and potency of final product of each reaction. Yield, which was not corrected for potency, was determined by the total weight of ending materials recovered as a percent of the theoretical yield which would result from complete conversion of the starting materials to dirithromycin. Potency was determined by the area under an HPLC tracing and reflects the amount of dirithromycin as a percent of the total weight of ending materials recovered. A measure of related substances was also determined by HPLC and is equal to the amount of ending materials, other than dirithromycin, as a percent of the total weight of ending materials recovered.

TABLE 2

| Example No. | Acid eq | Acetal eq | Acetonitrile % water | Yield % | Potency % | Related substances % |
| --- | --- | --- | --- | --- | --- | --- |
| 1 | 0.02 | 2.50 | 4 | 83.14 | 95.41 | 1.73 |
| 2 | 0.02 | 2.70 | 4 | 84.64 | 95.50 | 1.67 |
| 3 | 0.04 | 1.80 | 2 | 60.24 | 80.25 | 32.10 |
| 4 | 0.04 | 1.80 | 4 | 78.24 | 94.47 | 2.18 |
| 5 | 0.04 | 1.80 | 6 | 74.47 | 94.09 | 1.60 |
| 6 | 0.04 | 2.24 | 2 | 66.00 | 72.02 | 2.22 |
| 7 | 0.04 | 2.24 | 4 | 78.66 | 94.08 | 2.39 |
| 8 | 0.04 | 2.70 | 2 | 73.74 | 93.16 | 3.95 |
| 9 | 0.04 | 2.70 | 4 | 81.30 | 94.30 | 1.95 |
| 10 | 0.04 | 2.70 | 6 | 76.68 | 95.09 | 1.85 |
| 11 | 0.04 | 2.50 | 3 | 81.34 | 95.59 | 1.79 |
| 12 | 0.08 | 1.80 | 2 | 59.07 | 81.94 | 31.22 |
| 13 | 0.08 | 1.80 | 4 | 74.43 | 94.26 | 2.67 |
| 14 | 0.08 | 2.24 | 2 | 64.09 | 75.09 | 1.85 |
| 15 | 0.08 | 2.24 | 4 | 77.34 | 95.03 | 2.04 |
| 16 | 0.08 | 2.24 | 6 | 73.23 | 94.58 | 1.83 |
| 17 | 0.08 | 2.70 | 2 | 91.00 | 93.20 | 3.10 |
| 18 | 0.08 | 2.70 | 4 | 75.74 | 94.58 | 1.87 |

TABLE 2-continued

| Example No. | Acid eq | Acetal eq | Acetonitrile % water | Yield % | Potency % | Related substances % |
|---|---|---|---|---|---|---|
| 19 | 0.12 | 1.80 | 2 | 59.56 | 97.34 | 5.16 |
| 20 | 0.12 | 1.80 | 6 | 71.81 | 94.27 | 1.66 |
| 21 | 0.12 | 2.24 | 4 | 72.07 | 94.38 | 2.24 |
| 22 | 0.12 | 2.70 | 2 | 66.18 | 92.27 | 4.87 |
| 23 | 0.12 | 2.70 | 6 | 69.93 | 94.64 | 1.89 |

Preparation 2

Crystalline dirithromycin—a condensation product of 2-(2-methoxyethoxy)acetaldehyde diethyl acetal and erythromyclamine Several reactions were conducted essentially as outlined in Preparation 1 above but 2-(2-methoxyethoxy)-acetaldehyde diethyl acetal was used instead of the dimethyl acetal. The hydrolysis reaction, again using p-toluenesulfonic acid as catalyst, was allowed to reach equilibrium at 23° C. before erythromycylamine (5 g, 1 eq) was added. Dirithromycin crystals were recovered as previously described. Table 3 contains the specific reaction conditions and reports the yield and potency of final product of each reaction.

TABLE 3

| Example No. | Acid eq | Acetal eq | Acetonitrile % water | Yield % | Potency % | Related substances % |
|---|---|---|---|---|---|---|
| 24 | 0.10 | 1.50 | 2.00 | 73.74 | 92.29 | 3.07 |
| 25 | 0.10 | 1.50 | 3.30 | 73.75 | 94.51 | 2.17 |
| 26 | 0.12 | 2.00 | 0.00 | 55.48 | 3.06 | |
| 27 | 0.12 | 2.00 | 1.30 | 70.27 | 87.13 | 10.04 |
| 28 | 0.12 | 2.00 | 3.30 | 74.85 | 89.51 | 7.45 |

EXAMPLE 29

Crystalline dirithromycin—a condensation product of 2-(2-methoxyethoxy)acetaldehyde dimethyl acetal and erythromycylamine Further reactions were conducted for the synthesis of dirithromycin according to the following procedure. 2-(2-Methoxyethoxy)acetaldehyde dimethyl acetal (12 g, 2.7 eq) was placed in a three-neck flask equipped with a mechanical stirrer and dissolved in 60 ml of acetonitrile containing 4% water. p-Toluenesulfonic acid (200 mg, 0.04 eq) was added and the mixture was stirred under a nitrogen atmosphere for 3 hours at 30° C., after which, the temperature was adjusted to 23° C. Erythromycylamine (20 g, 1 eq) was added over a 20 minute period and stirring continued for 12–16 hours at 23° C. The reaction mixture was cooled to 0° C. for 2 hours and then filtered to recover dirithromycin crystals. The crystals were washed with cold acetonitrile and dried in vacuo at 40° C. The yield of final product was 84.5% with a potency of 95.4% (average of three reactions).

crystalline dirithromycin—a condensation product of 2-(2-methoxyethoxy)acetaldehyde dimethyl acetal and erythromycylamine Several large scale reactions were conducted according to the following procedure. A 500 gallon glass-lined reactor was charged with 200 L acetonitrile, 9 L deionized water and 45.2 kg (2.7 eq) 2-(2-methoxyethoxy)-acetaldehyde dimethyl acetal. About 10L acetonitrile was used to rinse in the acetal. To this solution was added 750 g ( 0.04 eq) p-toluenesulfonic acid and the solution was stirred at a temperature between 23° to 25° C. for the time necessary for the reaction to reach an acetal/hemiacetal equilibrium 14 to 21 hours. The slurry was cooled to between 0° and 5° C., stirred for two hours, filtered, and rinsed with 90 L acetonitrile which had been chilled to between 0° and 5° C. The product was dried in vacuo at a temperature less than 65° C. The yield of final product was 83.6% with a potency of 95.9% (average of four reactions).

I claim:

1. A process for making crystalline dirithromycin comprising the steps of:
   (a) dissolving in aqueous acetonitrile an acetal, represented by the formula

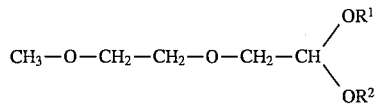

wherein $R^1$ and $R^2$ are straight or branched alkyl groups of one to about six carbon atoms which may be identical to or different from each other or together with each other may be $-CH_2-CH_2-$, $-CH_2-CH_2-CH_2-$, or $-CH_2-CH_2-CH_2-CH_2-$ thereby forming a 5-to 7-membered ring when taken in conjunction with the structure to which they are attached
   (b) hydrolyzing the product of step (a) over time in the presence of an acid catalyst thereby forming a hemiacetal; and
   (c) reacting the hemiacetal of step (b) with erythromycylamine thereby forming crystalline dirithromycin, wherein the entire process is capable of being carried out in situ.

2. A process of claim 1 wherein the acetal is 2-(2-methoxyethoxy)acetaldehyde diethyl acetal or 2-(2-methoxyethoxy)acetaldehyde dimethyl acetal.

3. A process of claim 1 wherein the water content of the acetonitrile solvent is from about 2% to about 10%.

4. A process of claim 1 wherein the water content of the acetonitrile solvent is from about 3% to about 5%.

5. A process of claim 1 wherein the water content of the acetonitrile solvent is about 4%.

6. A process of claim 1 wherein the acid catalyst is sulfuric acid, methanesulfonic acid, p-toluenesulfonic acid, hydrochloric acid, or camphorsulfonic acid.

7. A process of claim 1 wherein the acid catalyst is p-toluenesulfonic acid.

8. A process of claim 1 wherein the molar equivalents of acetal, measured relative to the amount of erythromycylamine, range from about 1.5 to about 3.5.

9. A process of claim 1 wherein the molar equivalents of acetal, measured relative to the amount of erythromycylamine, is about 2.7.

10. A process of claim 1 wherein the molar equivalents of acid catalyst, measured relative to the amount of erythromycylamine, is less than about 0.2.

11. A process of claim 7 wherein the molar equivalents of acid catalyst, measured relative to the amount of erythromycylamine, is about 0.04.

12. A process of claim 2 wherein the water content of the acetonitrile solvent is about 4%.

13. A process of claim 2 wherein the acid catalyst is p-toluenesulfonic acid.

14. A process of claim 2 wherein the molar equivalents of acetal, measured relative to the amount of erythromycylamine, is about 2.7.

15. A process of claim 13 wherein the molar equivalents of acid catalyst, measured relative to the amount of erythromycylamine, is about 0.04.

16. A process of claim 12 wherein the acid catalyst is p-toluenesulfonic acid.

17. A process of claim 12 wherein the molar equivalents of acetal, measured relative to the amount of erythromycylamine, is about 2.7.

18. A process of claim 16 wherein the molar equivalents of acid catalyst, measured relative to the amount of erythromycylamine, is about 0.04.

19. A process of claim 16 wherein the molar equivalents of acetal, measured relative to the amount of erythromycylamine, is about 2.7.

20. A process of claim 19 wherein the molar equivalents of acid catalyst, measured relative to the amount of erythromycylamine, is about 0.04.

21. A one-pot process for making crystalline dirithromycin comprising the steps of:

(a) dissolving in aqueous acetonitrile having a water content of from about 2% to about 10% an acetal, represented by the formula

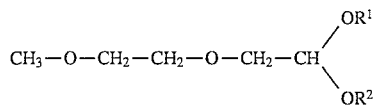

wherein $R^1$ and $R^2$ are straight or branched alkyl groups of one to about six carbon atoms which may be identical to or different from each other or together with each other may be —$CH_2$—$CH_2$—, —$CH_2$—$CH_2$—$CH_2$—, or —$CH_2$—$CH_2$—$CH_2$—$CH_2$— thereby forming a 5- to 7-membered ring when taken in conjunction with the structure to which they are attached; (b) hydrolyzing the product of step (a) over time in the presence of an acid catalyst thereby forming a hemiacetal; and (c) reacting the hemiacetal of step (b) with erythromycylamine thereby forming crystalline dirithromycin, wherein the molar equivalents of acid catalyst, measured relative to the amount of erythromycylamine, is less than about 0.2, and wherein the molar equivalents of acetal, measured relative to the amount of erythromycylamine, range from about 1.5 to about 3.5.

22. A process for making crystalline dirithromycin comprising:

reacting a hemiacetal with erythromycylamine in aqueous acetonitrile having a water content of from about 2% to about 10% thereby forming crystalline dirithromycin, wherein the hemiacemal is prepared by dissolving in aqueous acetonitrile having a water content of from about 2% to about 10% an acetal, represented by the formula

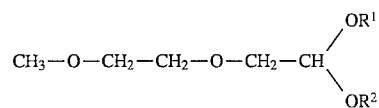

wherein $R^1$ and $R^2$ are straight or branched alkyl groups of one to about six carbon atoms which may be identical to or different from each other or together with each other may be —$CH_2$—$CH_2$—, —$CH_2$—$CH_2$—$CH_2$—, or —$CH_2$—$CH_2$—$CH_2$—$CH_2$— thereby forming a 5- to 7-membered ring when taken in conjunction with the structure to which they are attached, and hydrolyzing over time in the presence of an acid catalyst, wherein the molar equivalents of acid catalyst, measured relative to the amount of erythromycylamine, is less than about 0.2, and wherein the molar equivalents of acetal, measured relative to the amount of erythromycylamine, range from about 1.5 to about 3.5.

* * * * *